United States Patent [19]
Woloshuk et al.

[11] Patent Number: 5,856,151
[45] Date of Patent: Jan. 5, 1999

[54] ANTIFUNGAL PREPARATIONS CONTAINING OSMOTIN

[75] Inventors: Charles Peter Woloshuk, Raleigh, N.C.; Leo Sjoerd Melchers, Leiden, Netherlands; Bernardus Johannes Clemens Cornelissen, Warmond, Netherlands; Elisabeth Josine Sophie Meulenhoff, Amsterdam, Netherlands; Petrus Josephus Maria Van Den Elzen, Voorhout, Netherlands

[73] Assignee: Mogen International, N.V., Leiden, Netherlands

[21] Appl. No.: 315,868

[22] Filed: Sep. 30, 1994

Related U.S. Application Data

[62] Division of Ser. No. 828,798, Apr. 6, 1992, Pat. No. 5,389,609, which is a division of PCT/NL91/00089 May 31, 1991.

[30] Foreign Application Priority Data

Jun. 7, 1990 [NL]  Netherlands ............................ 9001293

[51] Int. Cl.$^6$ ............................ C12N 15/00; C12P 27/06; A61K 38/00; C07K 14/00
[52] U.S. Cl. ............................ 435/172.3; 435/69.1; 514/2; 530/370; 800/205; 800/DIG. 42; 800/DIG. 43
[58] Field of Search ................................ 514/2; 530/370; 435/172.3, 69.1; 800/205, DIG. 42, DIG. 43

[56] References Cited

U.S. PATENT DOCUMENTS 5,389,609  2/1995  Woloshuk et al. ......................... 514/12

OTHER PUBLICATIONS

Singh et al. Molecular cloning of osmotin and regulation of its expression by ABA and adaptation to low water potential. Plant Physiology. 90:1096–1101, 1989.

Lund et al. Bacterial chitinase is modified and secreted in transgenic tobacco. Plant Physiology. 91:130–135, 1989.

Thaumtin–Like Pathogenesis—Related Proteins are Antifungal Alison J. Vigers, Plant Sci, 83(1992) 155–161.

A New Family of Plant Antifungal Proteins Alison J. Vigers, Molec. Plant—Microbe Interactions vol. 4 No. 4 pp. 315–323 1991.

Antifungal Activity of Tobacco Osmotin . . . Laura R. Abad, Plant Science 118 (1996) 11–23.

Roberts et al, "Isolation and Partial Characterization of Two Anti–Fungal Proteins From Barley", Biochimica et Biophysica Acta 880(1986) 161–170.

Dayhoff et al, Protein Segment Dictionary pp. v–vii and 1 (1978).

Lipman et al, "Rapid and Sensitive Protein Similarity Searches", Science vol. 227, pp. 1435–1441 (1985).

*Primary Examiner*—Douglas W. Robinson
*Assistant Examiner*—Thanda Wai
*Attorney, Agent, or Firm*—Ladas & Parry

[57] ABSTRACT

A method for inhibiting the growth and/or germination of a fungus that is susceptible to an osmotin protein by contacting the fungus, or causing the fungus to be contacted with, an effective amount of an osmotin protein. The fungus can be, for example, a plant pathogenic fungus, such as an Oomycete. In one embodiment of the invention, the effective amount of the osmotin protein is produced by a plant having incorporated into its genome a chimeric gene having a) an open reading frame encoding the osmotin protein, or a precursor of the osmotin protein, and having operably linked thereto b) a regulatory region which causes the chimeric gene to be expressed in the plant.

19 Claims, 2 Drawing Sheets

5,856,151

ANTIFUNGAL PREPARATIONS CONTAINING OSMOTIN

This is a divisional of application Ser. No. 07/828,798, filed on Apr. 6, 1992, now U.S. Pat. No. 5,389,609, and the International Application PCT/NL91/00089, filed on May 31, 1991, and which designated the U.S.

TECHNICAL FIELD

The invention is related to inhibition of fungal growth using proteins that are isolated from plants. The invention provides processes for the preparation of such proteins in active form, as well as functional formulations thereof.

The invention also comprises plants with reduced susceptibility to fungi, characterized in that a gene or genes encoding such a protein are expressed constitutively or in a specifically regulated fashion in one or more parts of the plant, as well as processes for obtaining such plants.

BACKGROUND OF THE ART

Plant proteins with antifungal activity are known. A chitinase purified from bean causes inhibition of the growth of the fungus *Trichoderma viride* (Schlumbaum et al., (1986), Nature 324, 365–367).

A pea chitinase with a growth inhibitory effect on *Trichoderma viride* in agar plate tests is described by Mauch et al., (1988, Plant Physiol. 88, 936–942). This enzyme, however, only has a limited effect on for instance the ascomycete *Cladosporium cucumerinum*, and no effect on the growth of inter alia the Oomycetes *Phytophthora cactorum, Pythium aphanidermatum,* and *Pythium ultimum.* Hence, an important disadvantage of this enzyme is its limited working range. In a similar test it was established that $\beta$-1,3-glucanase has a growth inhibitory effect on *Fusarium solani* f.sp. pisi.

A preparation with a hydrolytic effect on isolated cell walls of *Verticillium alboatrum,* comprising a combination of a purified endo-$\beta$-1,3-glucanase from tomato and an exo-$\beta$-1,3-glucanase from fungal origin is described by Young & Pegg (1982, Physiol. Plant Pathol. 21, 411–423). Both enzymes had no effect on their own.

Several thionines, inter alia from leaves of barley, maize, wheat, rye, and several dicotyledonous plants, showing a significant antifungal effect in in vitro tests, are described by Bohlmann, H. et al., (1988, EMBO J. 7, 1559–1565).

Furthermore, plant proteins with an enhancing effect on the fungus-inhibitory activity of antibiotics are described in International Patent Application PCT/US88/03420. These plant proteins are generally designated as Synergistic Antifungal Proteins or SAFPs. SAFPs are used in combination with polyoxines and nikkomycines, that are active on their own against phytopathogenic fungi; in combination with SAFPs improvements of the effectivity can be achieved in the order of 10 to 100. SAFPs have no antifungal effect on their own.

In plants, the synthesis of chitinases and glucanases, as well as a large number of different so-called pathogenesis-related (PR-) proteins, is known to be accompanied by a phenomenon known as the hypersensitive response, which is inter alia triggered by an incompatible plant pathogen. This hypersensitive response eventually results in resistance of the plant against a broad range of pathogens. Similarly, the synthesis of PR-proteins can be induced by a number of biotic and abiotic factors, such as fragments of fungal cell walls, chemical inducers, such as salicylate and the like, which also results in a broad pathogen-resistance of the plant. This resistance obtained through induction either by an incompatible pathogen or a biotic or abiotic factor, or chemical substance, is called 'induced resistance'. Although still very much has to be learned about induced resistance and the role of these PR-proteins, some classification has been done. In tobacco, it seems that at least 5 classes of PR-proteins are induced upon treatment with tobacco mosaic virus (TMV). This classification is based on features such as molecular weight, serological relationship, amino-acid sequence homology, and if known, enzymatic activity. Within these classes a division can be made into intracellular and extracellular proteins, which except for their cellular localisation in the plant, correspond to each other with respect to the features just mentioned (vide for overview, Bol J. F. et al., 1990, Annu. Rev. Phytopathol. 28, 113–138.) Since these proteins are believed to be somehow involved in pathogen resistance, a great deal of effort is put into identification of potent antipathogenic proteins within the family of PR-proteins.

Upto the present, the approach for the screening and isolation of antifungal proteins is the screening of PR-proteins with already known properties, such as molecular weight, pI, or enzymatic activity. This especially holds for the chitinases and $\beta$-1,3-glucanases, the substrates of which occur in the cell walls or integuments of most pathogens and/or pests. One disadvantage of this approach is that there seems to be no or little correlation between enzymatic (i.e. chitinase and glucanase) activity and antifungal effect, resulting in the often tedious isolation of proteins which turn out to have no significant antifungal effect. The second disadvantage is the even greater difficulty of isolating PR-proteins of which no activity or function is known, which is the case for the majority of the PR-proteins.

Therefore, there is a need for a more effective and reliable method to obtain proteins with a significant antipathogenic effect against a selected pathogen.

SUMMMARY OF THE INVENTION

The present invention provides a method for obtaining proteins with an antipathogenic activity. The present invention further provides antipathogenic proteins, in particular antifungal proteins, obtained by said methods. Also new antifungal preparations are provided comprising an antifungal protein according to the invention.

Furthermore, the present invention provides plants which show reduced susceptibility to fungi, due to the expression of an open reading frame encoding an antifungal protein according to the invention. In a preferred embodiment production of an antifungal protein in a plant is accompanied by targetting of the antifungal protein to the extracellular space, causing an enhanced antifungal effect.

DESCRIPTION OF THE FIGURES

The following figures further illustrate the invention.

DESCRIPTION OF THE INVENTION

Figure 1:
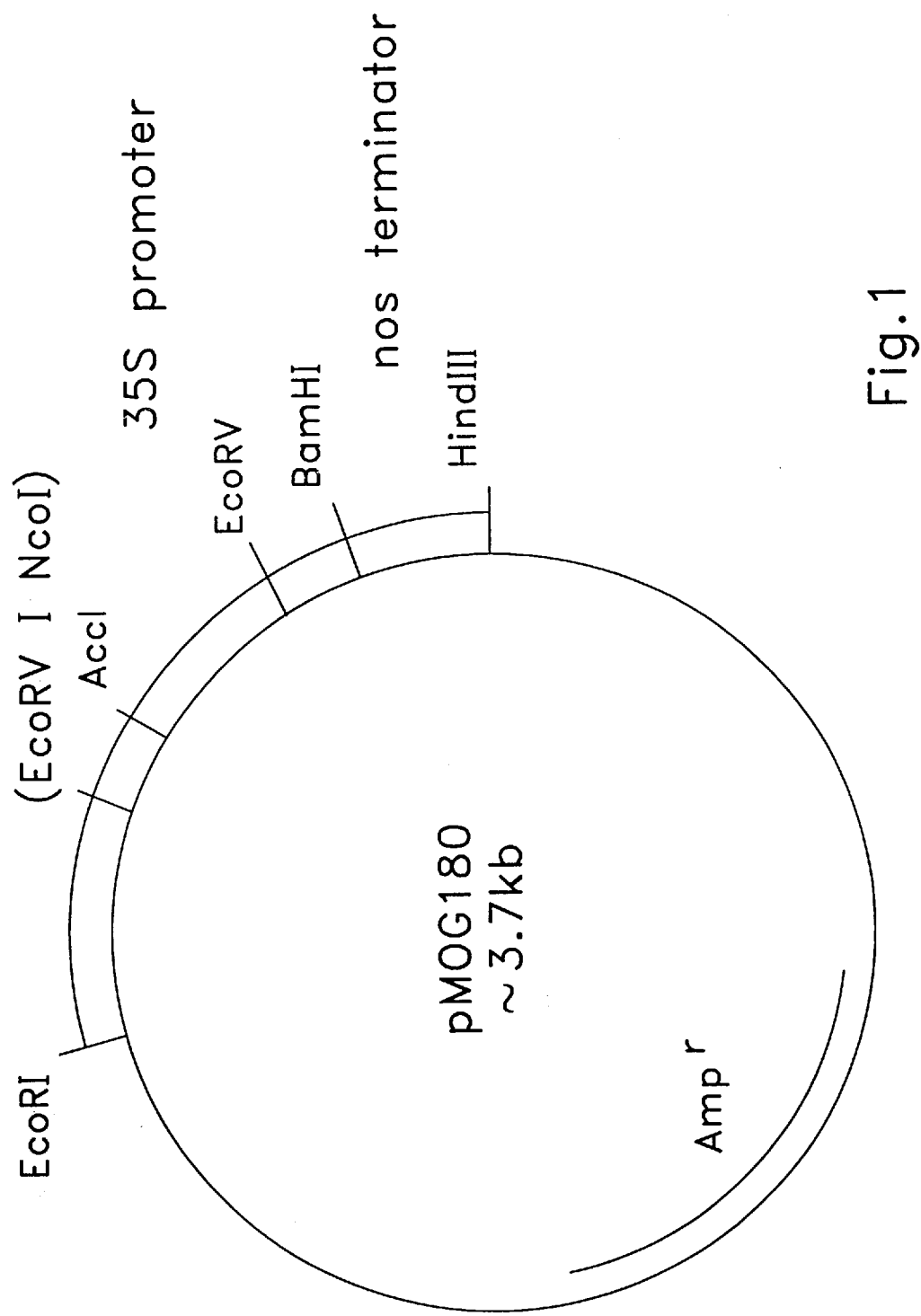
FIG. 1 shows schematically the expression vector pMOG180.
Figure 2:
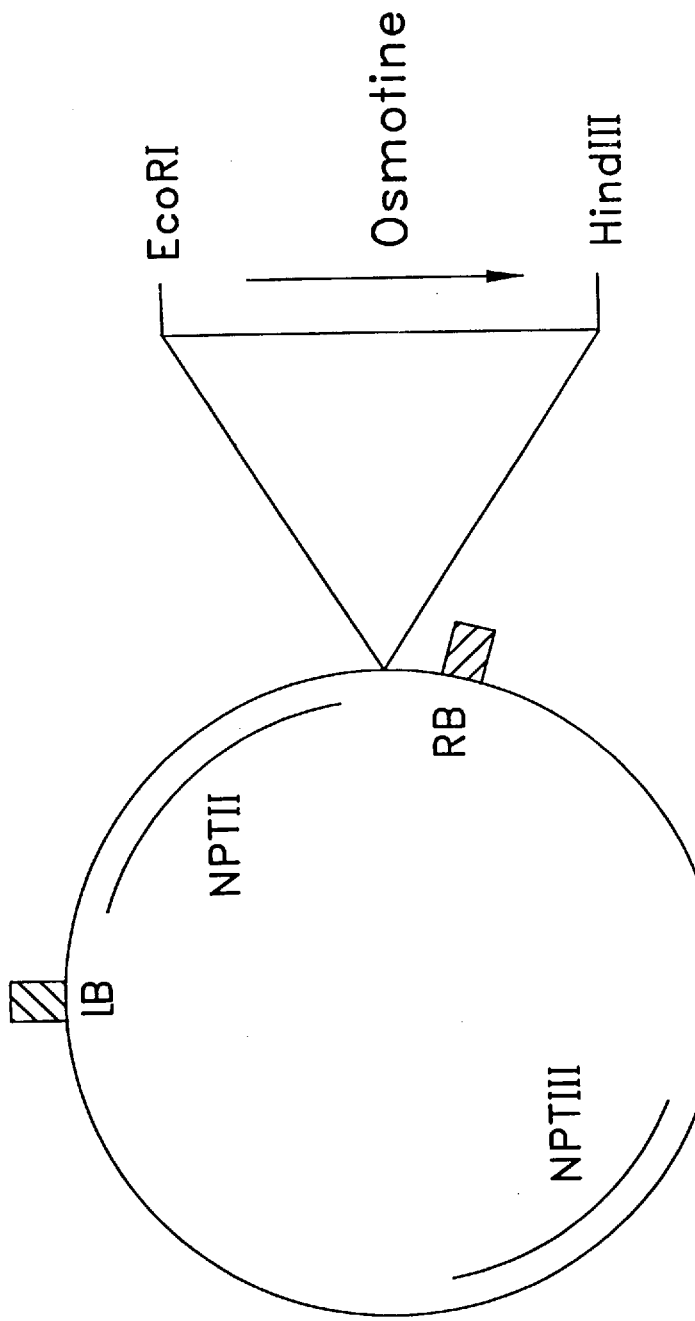
FIG. 2 shows the binary vector pMOG404; LB=left border, RB=right border of the T-DNA.

The present invention provides new methods for obtaining an antipathogenic protein from a plant comprising the steps of:

1) preparing an extract of a plant that shows induced resistance, 2) testing the extract for the presence of an antipathogenic activity in an antipathogenic assay, 3) purifying the antipathogenic activity by fractionating the extract using a protein purification method and an antipathogenic assay, 4) verifying the proteinaceous nature of the antipathogenic activity.

The word pathogen as used hereinafter is meant to comprise any organism capable of causing disease or otherwise affecting the plant such as reducing the growth, development, biomass, viability, nutritional value, or attractiveness of the plant, and which includes nematodes, fungi, bacteria, viruses and pests such as insects.

An antipathogenic assay is held to comprise a test for the antipathogenic effect of an extract or fraction by administering an aliquot of the said extract or fraction to the medium, or adding it to the food offered to the pathogen, in or on which the pathogen is allowed to germinate and/or develop and/or grow, under circumstances conducive to the germination and/or growth and/or development of the pathogen, and score for an antipathogenic effect due to the presence of the said fraction.

In a preferred embodiment of the invention a method is provided for obtaining antifungal proteins from plants, comprising the following steps:

1) treating a plant with an incompatible pathogen, a biotic or abiotic factor causing induced resistance in the said plant;

2) preparing a leaf-extract from the said plant;

3) desalting the leaf-extract, and incubating the leaf-extract at 4° C. temperature, 4) centrifuging the incubated leaf-extract, 5) testing an aliquot of the supernatant of the leaf-extract obtained after centrifugation in step 4 for the presence of an antifungal activity, by incubating the said supernatant in the presence of the fungus against which an antifungal protein is to be found, under conditions that are suitable for the growth and/or germination of the said fungus, and comparing the growth and/or germination of the fungus with an incubation without the antifungal activity;

6) fractionating the said supernatant using one or more non-denaturing protein fractionation methods, and 7) selecting fractions containing antifungal activity by testing an aliquot of the fractions as described for the supernatant in step 5), 8) further purifying said selected fractions using one or more non-denaturing protein fractionation methods, 9) if necessary repeating steps 7) and 8), until the antifungal protein is substantially free of other proteins.

During the purification, the antifungal activity can be tested for its proteinaceous nature by heating and/or protease treatment, and the like. If possible, after sufficient purification of the antifungal activity and after establishment that it is a protein, some of its physical parameters may be determined, such as molecular weight, isoelectric point, hydrophobicity, enzymatic activity and the like, to more selectively choose the next fractionation or purification technique, in order to obtain the best purification result. The choice of the optimal (combination of) protein purification techniques, based on the physical parameters such as mentioned above, is well within reach of a person skilled in protein purification. Putatively, depending for instance on the plant-material used and the antifungal protein actually purified, the establishment of the optimal conditions may require some trial and error, which is not to be regarded as undue experimentation.

Once the antifungal protein is reasonably pure its working range can be tested on other fungi, which may be other plant pathogenic fungi, animal or human pathogenic fungi, bacteria, nematodes and the like. In each and every individual case the concentration, pH, and ionic strength may be determined that is optimal for its stability and/or antifungal effect.

The method may be applied using different plant material in step 1, including other parts of the same plant, such as root-material, stem-material and the like, as well as a different plant variety or species. It is preferred to choose a plant line, variety, or species that shows induced resistance.

When the antifungal protein is substantially free from other protein and/or other subtances, the (partial) amino-acid sequence of the antifungal protein may be determined. Back-translating the amino-acid sequence to nucleotide sequences, a set of probes can be chemically synthesised to isolate cDNAs or genomic clones, encoding (part of) the antifungal protein, which can in principle be used for engineering of plants with reduced susceptibility to fungi. To this end an open reading frame, such as a cDNA- or DNA-fragment encoding (part of) the antifungal protein is suitably associated with elements required for expression in a plant cell. If the antifungal protein is an intracellular protein, the open reading frame may be altered to provide, upon expression, targetting of the protein to the extracellular space.

For purposes of illustration, the principle of the invention is set out in more detail below, taking the isolation and identification of an osmotin-like protein, as well as the subsequent cloning of a cDNA encoding this protein as a typical example. Moreover, this typical example also shows a method to obtain a transgenic plant with reduced susceptibility to fungi, by virtue of a high-level expression of an open reading frame, encoding a said osmotin-like protein in the said plant. In an especially preferred embodiment of the invention, it is shown how this normally intracellular osmotin-like protein is targetted to the extracellular space, thereby causing an enhanced antifungal effect in the plant in which it is produced.

It is to be understood that where osmotin-like proteins are mentioned explicitly, they merely serve to illustrate the principle of the method according to the invention and its result, and do not intend to limit the scope of the invention to osmotin-like proteins as such. Therefore, other antifungal proteins that can be obtained according to the presented method are held to be comprised by the present invention as well.

It was found that when plants are treated with an incompatible pathogen causing a hypersensitive response, a few days after the inoculation leaf extracts can be made from which fractions can be obtained that exhibit a strong antifungal effect. It was found in a number of fractions obtained from tobacco and tomato that the inhibitory effect on fungal growth could not be attributed to $\beta$-1,3-glucanases or chitinases, as in the further purified fractions with antifungal activity no glucanase or chitinase activity could be detected at all. The antifungal activity appeared heat-labile. The active component from tobacco was identified as a hydrophobic protein with a molecular weight of about 24 kD and a basic isoelectric point (pI) and was called AP20 (also referred to as AP24). After purification and determination of the amino-acid sequence of the N-terminus of AP20, this part appeared identical to the corresponding part of osmotin, a protein known to occur in tobacco (Singh, N. K. et al., (1987) Plant Physiol. 85, 529–536; Sing, N. K. et al., (1989), Plant Physiol. 90, 1096–1101) and which belongs to a group of proteins designated as osmotins, or alternatively as osmotin-like proteins. Osmotin-like proteins obtained their name because of the finding that they are synthesized inter alia during osmotic adaptation of plant cells in a medium containing high concentrations of sodium chloride, potassium chloride or polyethylene glycol; however, accumulation of osmotin-like proteins seems to be dependent on the continuous presence of osmotic agents. Under the influence of (some) non-osmotic agents like cadmium chloride accumulation does not occur (King et al., (1986), Plant Mol. Biol. 7, 441–449).

In tobacco two osmotins have been described, osmotin-I a water-soluble form, and osmotin-II, a detergent-soluble, relatively protease resistant form. Both osmotins from tobacco have a molecular weight of about 24 kD, show a large amino-acid sequence identity, as well as similarity with a 24 kD osmotin-like protein from tomato (*Lycopersicon esculentum*), and to other proteins, including thaumatin from *Thaumatococcus daniellii*, pathogenesis-related protein S (PR-S) from tobacco, and a bifunctional maize trypsin/α-amylase inhibitor. Osmotin-like proteins, which are all serologically related and have a molecular weight corresponding to those of osmotins from tobacco and tomato are described, inter alia, for millet, soybean, carrot (*Daucus carota*), cotton, potato (*Solanum tuberosum*) (Singh et al., (1987), P.N.A.S. USA 84,, 739–743), alfalfa (*Medicago sativa*), and bean (Phaseolus) (King et al., (1986), supra).

Up to now no effect of osmotin was known. It was generally assumed that osmotins function in providing the plant with osmotic tolerance after exposure to a low water potential (vide for instance Grosset et al., (1990) Plant Phys. 92, 520–527).

On the basis of the similarity of physical parameters, i.e. an almost identical molecular weight, an amino-acid sequence identical to that of osmotin-II from tobacco and almost identical to osmotin-I from tobacco and osmotin from tomato (NP24), as well as a corresponding pI, it was concluded that the antifungal protein AP20 actually is an osmotin. To test the assumption that an antifungal effect may be a general feature of osmotin-like proteins, we tested an osmotin-like protein from tomato, known as NP24, for its capacity to inhibit *P. infestans*. It appeared that NP24 possesses an antifungal effect as well.

Hence, it was concluded that osmotin-like proteins from tobacco and tomato possess antifungal activity and are therefore suitable for use in an antifungal preparation. Regarding the large homology between osmotin-like proteins in the plant kingdom, we predict other osmotins than those from tobacco and tomato to possess antifungal activity as well.

Osmotins or osmotin-like proteins are held to comprise proteins with an amino-acid sequence homology of more than 70% compared to osmotin from tobacco, preferably more than 80%, and a basic pI, synthesis of which is correlated with osmotic adaptation of plant cells to high NaCl containing media, which have an antifungal effect on at least one fungus. An antifungal effect is defined herein as any inhibitory action on germination, growth and/or differentiation of a fungus, or any other action causing a reduction of the viability and/or infectivity of the fungus.

Preferably, for the isolation of osmotins one will make use of the possibility to induce the synthesis of this protein, for example by inoculating the plant with an incompatible pathogen from the group consisting of viruses, bacteria or fungi. However, it is not necessary to inoculate plants with pathogens. Other ways of inducing osmotin synthesis can be applied, such as exposure of plants or cultured plant cells to NaCl and/or polyethyleen glycol. This leads to high concentrations of osmotin in the cell; accumulation levels upto 12% of total soluble protein have been reported (Singh et al., (1987) Plant Physiol., supra). Osmotin synthesis can also be induced by treating plants or plant cells with ABA (Abscisic Acid) (Singh et al., (1987) P.N.A.S., supra).

Plants from which osmotins can be isolated are inter alia, millet, soybean, cotton, tomato and potato, described by Singh et al., (1987), P.N.A.S. USA 84, 739–743; and King et al., (1988), Plant. Mol. Biol. 10, 401–412), but also osmotins (osmotin-like proteins) from other plants than those mentioned above will satisfy if they have sufficient homology with osmotin from tobacco, or have physical parameters that are comparable to those of osmotin from tobacco. In a preferred embodiment of the invention use is made of osmotin-like proteins isolated from material (including cell cultures) of a tobacco plant that is exposed to a stress-factor, such as an osmotic agent, drought, or a pathogen, preferably tobacco mosaic virus (TMV), or from a tomato plant inoculated with the fungus *Phytophthora infestans*, or with arachidonic acid.

For the isolation of osmotin-like proteins use can be made of (combinations) of generally known protein fractionation techniques, such as centrifugation, chromatography, electrophoresis and the like. For preparative purposes one will preferably use techniques which are based on non-denaturing conditions. In a preferred embodiment gel-chromatography and ion-exchange chromatography are used in combination with hydrophobic interaction chromatography, whereby elution is monitored with UV-spectroscopy. The obtained fractions can be analysed for the presence of the inhibitory effect on the growth of pregerminated or non-pregerminated spores of fungi that are susceptible to osmotin-like proteins, such as fungi of the genus Phytophthora, preferably *Phytophthora infestans*. The spores (between 1 and 100 spores per $\mu$l, preferably between 5 and 20 spores per $\mu$l) can be tested on a suitable feeding layer, such as potato dextrose agar (PDA) and the like. The development and the growth of the fungus can easily be determined after staining the mycelium at particular times after adding the fraction; upon comparison of incubations of fungal spores with a control preparation, the presence of the antifungal factor in the fraction can be determined. The fractions that show heat-labile antifungal activity can be analysed for the presence of osmotin-like proteins on the basis of molecular weight using electrophoresis and or immunoblot techniques using antibodies directed against e.g. osmotin from tobacco or pathogenesis-related protein S (PR-S). The fractions containing osmotin can be fractionated further using for instance Hydrophobic Interaction Chromatography (HIC) or High Performance Liquid Chromatography (HPLC); with these techniques almost absolute purity can be obtained. According to the process described here it is possible to isolate osmotin-like proteins from any plant material containing said proteins.

For purposes of inhibition of fungal growth osmotins can for instance be applied for the preservation of foodstuffs, in cosmetics, as a pharmaceutical or medicament, be used in water for spraying indoor plants and agricultural crops, be used for the preservation of fruit, vegetables and other crops which may be stored for a limited period of time and in all those cases in which fungal growth is to be inhibited, under circumstances conducive to osmotins. Hereby, osmotin may be added per se or in combination with a suitable carrier, or if desired, in combination with other antifungal substances, in the form of powders, granulates, aerosols, solutions, gels or other solvents or carrier materials.

For application in preparations, e.g. to broaden the working range, also a combination of osmotin and other fungal inhibitory agents may be used, such as classical fungal antibiotics, SAFPs and chemical fungicides such as polyoxines, nikkomycines, carboxymides, aromatic carbohydrates, carboxines, morpholines, inhibitors of sterol biosynthesis, organophosphorus compounds, enzymes such as glucanases, chitinases, lysozymes and the like. Either per se, or in combination with other active constituents, osmotin should be applied in concentrations which are effective for the ultimate goal, in general between 1 $\mu$g/ml and 100 mg/ml, preferably between 5 $\mu$g/ml and 5 mg/ml, within pH boundaries of 3.0 and 9.0. In general it is desired to use buffered preparations, e.g. phosphate buffers between 1 mM and 1M, preferably between 10 mM and 100 mM, in particular between 15 and 50 mM, whereby in case of low buffer concentrations it is desired to add a salt to increase ionic strength, preferably NaCl in concentrations between 1 mM and 1M, preferably 10 mM and 100 mM.

In a special embodiment of the invention transgenic plants are obtained which have reduced susceptibility to fungi, by virtue of the constitutive expression in one or more of the plant's parts, of one or more genes that code for an osmotin (-like) protein, or by virtue of simultaneous constitutive expression of a combination of an osmotin gene and, e.g. a glucanase and/or a chitinase gene or the like, in one or more parts of the plant. In addition to genes occuring in tobacco, described by Singh et al., (1987, Plant Physiol., supra) and tomato, i.e. the gene coding for NP24, described by King et al., (1988, Plant Mol. Biol., supra) also osmotin genes occurring in inter alia millet, soybean, potato, tomato, carrot, cotton and the like may be used for this purpose. Using known techniques, it is state of the art knowledge how to obtain genes or cDNAs that code for osmotin-like proteins from different plant species, with the aid of a polynucleotide probe such as a gene fragment of an osmotin gene from tobacco, or a synthetic oligonucleotide probe based on a known sequence of an osmotin gene. Using commonly known techniques a skilled person is capable of amplifying the obtained osmotin gene fragment, determining the nucleotide sequence of the DNA fragment, and cloning the gene fragment or CDNA in the proper orientation into a vector containing sequences which are necessary for the desired expression of the gene fragment in one or more parts of the plant. If such an expression construct is suitably administered to plant material this will result in transformed plant material, which in turn can be used to (re)generate whole transformed plants that express the gene or gene fragment encoding (part of) the osmotin protein in some or all plant parts.

A preferred method of isolating a DNA fragment comprising (part of) the coding region of an osmotin gene makes use of the polymerase chain reaction (PCR) technology, which is described by Maniatis et al., (1989, in: *Molecular Cloning; A Laboratory Manual,* 2nd. edition, Cold Spring Harbor Laboratory Press). Starting with the published nucleotide sequences of an osmotin gene, or the nucleotide sequence deduced from a known amino-acid sequences of an purified osmotin, any desired gene fragment can be obtained by e.g. producing synthetic oligonucleotides that are complementary to the ultimate 5' and 3' regions of the desired fragment. By allowing these oligonucleotides as polymerisation primer to hybridise in vitro with plant DNA or a cDNA-library (preferably obtained from plant cells that have been exposed to osmotic or pathogen stress) and conduct a number of polymerisation cycles, the desired fragment can be selectively amplified. The primers can be synthesised to contain internal restriction sites that correspond to the ends of linearised cloning vehicles, in order to provide for easy ligation of the amplified fragments into the vehicle. The isolated fragment can subsequently be cloned and manipulated further. Thus, even combinations of gene fragments derived from different osmotin-like protein genes, including entirely synthetic fragments of such genes, may be joined to form a single open reading frame encoding a chimeric osmotin-like protein.

To express the newly introduced protein in the plant a transcription promoter has to be included in the expression construct; use can be made, inter alia, of the CaMV 35S promoter, so-called T-DNA promoters, or plant promoters, optionally including one or more enhancer fragments. In general one will use a strong constitutive promoter that is functional in all or a large number of plant parts, although tissue-specific or developmentally regulated or otherwise controlable or inducible promoters may be used. A regulatable, e.g. a tissue-specific promoter may be advantageous if the phytopathogenic fungus for instance only affects particular parts of the plant, or only invades via particular plant parts. In addition to a promoter that is functional in plants and the coding sequence, still other regulatory elements may be included in the expression construct, such as transcriptional enhancers, translational enhancers, like the leader-sequence of the RNA genome of TMV (Gallie, D. R. et al., (1988), Nucl. Acids Res. 16, 883–893), mRNA-stabilising leader sequences, like the alfalfa mosaic virus (AlMV) RNA4-leader, introns, a transcription terminator and polyadenylation signal, like e.g. the nopaline synthase terminator (Tnos). It is known how these elements may be used in an expression construct, in order to influence the level of gene expression in a desired fashion. To obtain further optimisations of gene expression it may be desirable to use a genomic clone instead of a cDNA clone. Alternatively, if deemed desirable, a synthetic intron may be inserted into the cDNA sequence.

To obtain some fungus-inhibitory effect it is in principle sufficient if high constitutive or specifically regulated high expression of an osmotin-like protein gene in all or some of the parts of the transgenic plant is achieved. The wild-type osmotin-like protein formed is assumed to accumulate in the vacuoles of a plant cell. It was found that when the wild-type osmotin-like protein gene is expressed, an antifungal effect can be observed.

In a preferred embodiment of the invention an intracellular osmotin(-like) protein is targetted to the extracellular space as a consequence of the genetic alteration of the gene encoding it. One possible way to achieve this is the removal of approximately 20 C-terminal amino-acids of the wild-type primary translation product encoded by the osmotin mRNA, which appear responsible for intracellular localisation. Removal of the C-terminal part of the protein can be achieved for instance by the introduction of a translational stopcodon into the gene to prevent codons that are located more to the 3' end from being translated into amino-acids. As an alternative the amino-acid sequence of the C-terminal part of the osmotin-like protein may be altered with respect to the wild-type as to inhibit its proper functioning. The open reading frame may also be extended to provide for additional amino-acids to the C-terminal end of the wild-type osmotin, thus preventing proper functioning of the C-terminal resulting in targetting in extracellular targetting. The method by which the protein is targetted out of the cell is itself not critical to the invention, as long as alteration of the protein does not completely annul its antifungal effect.

It was found for instance in leaf-discs of tobacco, that targetting of the osmotin-like protein results in an appreciable enhancement of the antifungal effect on the fungus *P. nicotianae* var nicotianae.

It may be desirable in certain circumstances to obtain plants which express both a gene encoding a wildtype intracellular osmotin-like protein and a gene encoding a extracellularly targetted intracellular osmotin-like protein, to further enhance the antifungal effect.

Expression levels of the newly introduced gene-constructs may be determined by analysing total cellular proteins or proteins in the extracellular fluid, using the Western blot technique. Also in a known manner the (relative) amount of mRNA can be determined using the Northern blot technique, hybridising the blot with a probe directed to osmotin mRNA. Transformed plants with an apparently good expression level of a gene-construct encoding either the wild-type or the targetted osmotin-like protein can subsequently be tested for fungal resistance by inoculating the plant with a pathogenic fungus, whereupon the rate and severity of symptom development can be compared with that of non-transformed plants. An alternative method of testing the fungal resistance is testing the effect of the fungus on leaf-discs of transgenic plants rather than on whole plants. An advantage of this method is the relative ease of assessing symptom development in a more or less quantitative way.

The invention also comprises microorganisms transformed with a gene fragment encoding (part of) an osmotin-like protein for production of an osmotin-like protein, to obtain the osmotin-like proteins for use in antifungal preparations. Preferred microorganisms are for instance bacteria, e.g. Bacillus species, or yeasts. Alternatively, microorganisms transformed with a gene or gene fragment encoding an osmotin-like protein and which produce an osmotin-like protein may be used for the protection of plants if they are capable of growing on or in the presence of the said plant. Preferred microorganisms are for example Pseudomonas, or Rhizobium species. Expression of an osmotin-like protein cDNA fragment in *E. coli* has already been obtained by us.

Most embodiments of the invention in which plants are transformed with an osmotin-like protein gene-construct that is to be expressed in the plant require the use of several generally known microbiological, molecular biological, recombinant DNA, plant transformation and plant tissue-culture techniques, which are all within reach of the average skilled worker. Standard techniques for the isolation, manipulation and amplification of DNA, as well as suitable vectors for replication of recombinant DNA, suitable bacterium strains, selection markers, media and the like are described for instance in Maniatis et al., *molecular cloning: A Laboratory Manual* 2nd. edition (1989) Cold Spring Harbor Laboratory Press; DNA Cloning: Volumes I and II (D. N. Glover ed. 1985); and in: From Genes To Clones (E. -L. Winnacker ed. 1987).

Known vectors that can be used for cloning in bacteria are for instance pUC18 (vide in general From Genes to Clones, supra) and pEM.BL plasmids (Dente L., Nucleic Acids Research 11, 1645–1655). The latter plasmids have the advantage of carrying an origin of replication for particular single stranded DNA bacteriophages, so that plasmids which are propagated herein can be used directly for DNA sequencing according to the method of Sanger et al., (1980) J. Mol. Biol. 14, 161–178.

For the introduction of recombinant genes into the genome of plants several techniques are available, such as transformation using Agrobacterium, bombardment of plant-tissue with DNA-coated particles (Klein et al., 1987, Nature 327, 70–73) direct DNA uptake using e.g. the Calcium/PEG method (Krens F. A. et al., 1982, Nature, 296, 72–74), or microinjection of DNA into protoplasts (Crossway A. et al., 1986, Mol. Gen. Genet. 202, 179–185), and the like. For a general overview of plant transformation techniques see for example Lichtenstein et al., in: Genetic Engineering Vol. 6, 104–182; Rigby, editor, 1987). In two preferred embodiments of the invention use is made of the *Agrobacterium* binary vector system. The principle of the binary vector system is described by Hoekema et al., (1983), Nature 303, 179–180; Bevan et al., 1984, Nucl. Acids Res. 12, 8711–8721).

After introduction of the genetic material a whole new plant can be regenerated from the transformed cell (protoplast) or transformed tissue. Alternatively, pollen cells can be transformed and used for pollination of an acceptor plant. Selection of actually transformed plants can for instance be carried out if on the same DNA fragment on which the gene that is to be introduced is located, also harbours a marker gene. Marker genes can for instance encode herbicide or antibiotic resistance, or enzymes that are capable of catalysing a staining reaction, or coding an easily perceptible (e.g. directly visible) trait. Plants expressing the marker gene are likely to posess also the introduced osmotin-like protein gene. The selected plants can be analysed for expression of the osmotin-like protein gene using Western or Northern blot techniques known to researchers in the field. Fungal resistant plants can be selected from good expressors, by exposure of the plants to any fungus that causes a pathogenic effect on non-transformed plants of the same variety.

Using the above mentioned transformation techniques there are in principle no limitations to practicing the invention with respect to the host plant of choice. Both dicotyledonous plants (such as tomato, potato, bean, soybean, rapeseed, cotton and the like), as well as monocotyledonous plants (maize, wheat, barley, Asparagus, rice and the like) can be succesfully transformed using recombinant DNA, and regenerated into full grown seed producing plants expressing the recombinant DNA.

Preferred embodiments are tobacco, potato and tomato plants transformed with an osmotin gene from tobacco. However, it will be obvious that the invention can be applied to every crop plant that is susceptible to a fungus towards which osmotin shows an inhibitory effect.

All references cited in this specification are indicative of the level of skill in the arts to which the invention pertains. All publications, whether patents or otherwise, referred to previously or later in this specification are herein separately incorporated by reference.

The Examples given below are just given for purposes of enablement and do not intend in any way to limit the scope of the invention.

EXAMPLE 1

Isolation of AP20 from TMV-induced tobacco plants

Leaves of tobacco (*Nicotiana tabacum* cv. Samsun NN) of 7 to 8 weeks old plants were inoculated with tobacco mosaic virus (TMV), using a standard technique known to the skilled worker in the art. Seven days after inoculation 400 gram leaves was harvested and ogenized at 4° C. in 600 ml 0.5M NaOAc, 15 mM 2-mercapto-ethanol, and 4 gram active carbon, using a Waring bLendor. The homogenate was filtered over cheese cloth and subsequently, the filtrate was centrifuged at 5,000 g. The supernatant was centrifuged for 50 minutes at 22,000 g and desalted on a Sephadex G25 column (Pharmacia), length 60 cm, diameter 11.5 cm, and equilibrated in 20 mM NaOAc pH 5.2. The fraction containing proteins was stored overnight at 4° C. and subsequently centrifuged for 45 minutes at 22,000 g. The supernatant was passed through a S-sepharose "fast flow" (Pharmacia) column, length 5 cm, diameter 5 cm, which was equilibrated with 20 mM NaOAc pH 5.2, at a flow speed of approximately 15 ml per minute. The unbound proteins were collected. The bound proteins were eluted using an increasing linear NaCl gradient (0 to 500 mM) in the above mentioned buffer, and a flow speed of 3 ml per minute; fractions of 4.2 ml were collected. Each second fraction was analysed by electrophoresis using a 12.5% polyacrylamide gel in the presence of sodium dodecyl sulphate (SDS), using molecular weight markers of (20–66 kD) as reference. A separate portion of the same fractions was tested for antifungal effect.

For the testing of antifungal activity a microtiter dish assay was developed. Microtiter dishes both with 24 wells as with 96 wells were used. Subsequently, 250 $\mu$l (24 well dishes) or 50 $\mu$l (96 well dishes) potato dextrose agar (PDA) was pipetted into each well. Sporangia of $P.$ $infestans$ were suspended in water and added to the wells: 500–700 sporangia (in 50 $\mu$l) to the 24 well dishes, and 100–200 sporangia (in 25 $\mu$l) to the 96 well dishes. The portions of the fractions to be tested were dialysed against 15 mM $K_2HPO_4$/$KH_2PO_4$ pH 6.0, 20 mM NaCl, filter sterilised (0.22 $\mu$m filter) and added to the sporangia suspension (respectively 100 and 50 $\mu$l for the 24 well and the 96 well dishes). A low phosphate concentration appeared necessary, as $P.$ $infestans$ appeared sensitive to high concentrations; 15 mM potassium phosphate appeared to have no effect on the growth of $P.$ $infestans$. The addition of NaCl is desired for the stabilisation of the antifungal activity at low phosphate concentrations. As a control (portions of) the same fractions were boiled after dialysis for 10 minutes. Subsequently, the dishes were incubated in the dark at 20° C. for 4 to 5 days. The first signs of the fungus-inhibiting activity can already be observed under the microscope after about 20 hours. The fungus inhibiting effect is seen as lysis of the germinating sporangia and of the growing germ tubes or the hyphal tips. In a later stage also inhibition of mycelial growth can be observed.

For a further purification of the active component the active antifungal fractions were pooled, dialysed against 1M $(NH_4)_2SO_4$, 50 mM $K_2HPP_4$/$KH_2PO_4$ pH 7.0 and subsequently filtered over a 0.22 $\mu$m filter. Subsequently the filtrate was loaded onto a hydrophobic interaction column (HIC) (Phenylsuperose HR 5/5 from Pharmacia), which was previously equilibrated with dialysis buffer. All previous steps were carried out at 4° C.

The bound proteins were eluted with a decreasing $(NH_4)_2SO_4$ gradient (1M to 0M) in 50 mM $K_2HPO_4$/$KH_2PO_4$ pH 7.0, with a flow speed of 0.5 ml per minute at room temperature. The elution program was performed as follows:

in 5 minutes from 100 to 30% of the initial $(NH_4)_2SO_4$ concentration for 7.5 minutes of elution with 30% of the initial $(NH_4)_2SO_4$ concentration in 10 minutes from 30% to 0% of the initial concentration of $(NH_4)_2SO_4$.

The antifungal protein elutes from the column after about 5.5 minutes (app. 2.7 ml) at 0% of the initial $(NH_4)_2SO_4$ concentration; the antifungal protein in the peak fraction is of 95% purity. All these steps were carried out at room temperature. To obtain the antifungal protein in a 99% pure form, these fractions were dialysed against 1M $(NH_4)_2SO_4$, 50 mM $K_2HPO_4$/$KH_2PO_4$, pH 7 buffer and after filtration over a 0.22 $\mu$m filter, they were separated once more using the HIC column with the following elution program:

in 7.5 minutes from 100% to 15% for 12.5 minutes at 15% in 10 minutes from 15% to 0%.

The antifungal protein elutes from the column after 13 minutes (app. 2.7 ml); this eluate contains 99% pure protein. From 400 g leaf-material 400 $\mu$g of antifungal protein can be isolated (95% purity) or 200 $\mu$g antifungal protein of 99% purity. The antifungal protein with an estimated molecular weight of 24 kD was called AP20.

EXAMPLE 2

Elucidation of amino-acid sequence of AP20

The amino-acid sequence of the N-terminal part of AP20 was determined using techniques known to skilled persons in the art (vide for instance Matsudairo, P. et al., (1987), J. Biol. Chem. 262, 10035–10038). A comparison of partial amino-acid sequences of AP20 and osmotins from tobacco and tomato shows the complete identity of the 40 N-terminal amino-acid sequence of AP20 with that from the N-terminus of osmotin II from tobacco and a very high homology with osmotin I from tobacco and the osmotin-like protein NP24 from tomato.

A precise determination of the molecular weight of AP20 was carried out with the aid of 1D-polyacrylamide gel electrophoresis (1D-PAGE) using molecular weight references from 66 to 20 kD. According to this method the molecular weight was determined at 24 kD, which is well in agreement with the electrophoretic mobility of other osmotins.

The isoelectric point was determined with the aid of isoelectric focussing chromatography between pI 4.3 and 9.5. The mobility of AP20 in the used gel/buffer system did not allow an exact determination of the pI, as AP20 appeared to posses a higher pI value than the most basic marker (pH=9.5); it was concluded that the pI of AP20 is greater than 9.5. From a comparison of the physical parameters of AP20 with those from osmotins in tobacco and tomato (identical molecular weight, very basic pI, and identical amino-acid sequence of the 40 most N-terminal residues), it appears that AP20 is an osmotin. From the establishment of the antifungal effect of the isolated osmotin (AP20) isolated by us, and the high level of amino-acid sequence conservation between AP20 and the other osmotins, as well as between the osmotin. We predict more osmotin-like proteins in the plant kingdom will possess a similar antifurgal effect.

EXAMPLE 3

Isolation of osmotin from tomato and analysis of the antifungal effect on $P.$ $infestans$ The method that is used for the inoculation of tomato plants is described by Heller & Gessler (J. Pathology, 1986, 116, 323–328).

Two months old tomato plants ($Lycopersicon$ $esculentum$ cv. Moneymaker) were inoculated with zoospores of $P.$ $infestans$. The zoospores were formed in a suspension of $1 \times 10^5$ sporangia per ml incubation medium. Onto leaves an amount of 6 droplets of 10 $\mu$l of this suspension was pipetted per leaf. The plants were incubated at 15° C., at an air humidity of 95–100%, and low light-intensity, until the development of lesions became visible (after about 5 days). Subsequently, the temperature was increased to 22° C., air humidity was lowered to 75% and light intensity brought to normal. After another three days, the leaves with necrotic lesions were harvested and stored at −80° C.

The isolation procedure of osmotin from leaves of tomato (including the test on *P. infestans*) is similar to that of the isolation of AP20 from tobacco, as described in Example I.

Osmotin from tomato clearly has an inhibitory effect on the growth of *P. infestans*. In control experiments with osmotin that was heated to 100° C. or with buffer, no lysis could be observed.

EXAMPLE 4

Construction of pMOG180

To obtain high constitutive expression of osmotin genes in transgenic plants; an expression construct was made containing a strong promoter. To this end, the expression cassette from PROKI (Baulcombe et al., (1986), Nature 321, 446–449) was cloned as an EcoRI-HindIII fragment into pUC18. This cassette contains the CaMV 35S promoter on an EcoRI-BamHI restriction fragment and the nopaline synthase (nos) transcription terminator on a BamHI-HindIII fragment. The promoter fragment consists of the sequence from −800 to +1 of the CaMV genome, whereby position +1 is the transcription initiation site (Guilley et al., (1982), Cell 30, 763–773). From the literature it is known that duplication of the sequence between −343 and −90 increases the activity of the CaMV 35S promoter (Kay et al., (1987), Science 236, 1299–1302). To obtain a promoter containing a double 'expression enhancing fragment' (enhancer) the following cloning steps were carried out. First, the sequence upstream from the NcoI recognition site at position −512 was removed and the recognition site was itself changed into an EcoRI recognition site. To this end, the expression cassette in pUC18 was cut with NcoI, the obtained termini were filled in with Klenow polymerase and EcoRI-linkers were ligated to the termini.

The obtained plasmid was cut with EcoRI, resulting in deletion of the EcoRI fragment, and the termini were filled in with Klenow polymerase. Subsequently, the filled-in AccI-EcoRV promoter fragment (between −388 and −90) was cloned into the linear plasmid, whereby a new EcoRI site was created at the transition of the filled-in EcoRI and the filled-in AccI site. The newly obtained plasmid pMOG181 contains the CaMV 35S promoter, now with the double enhancer, in an expression cassette which is still lying on a EcoRI-HindIII fragment. Subsequently, from pMOG181 the derivate pMOG180 was made. Hereto, the vector was cut with BamHI, the termini thus obtained were filled-in with Klenow polymerase and a synthetic double-stranded DNA-fragment in the sequence protocol indicated as SEQID 1, containing the nucleotide sequence of the alfalfa mosaic virus RNA4 leader was cloned into the linear plasmid. After selection for the presence of a newly formed BamHI recognition site the pentanucleotide 5'-GGATC3' around the transcription initiation site was eliminated via in vitro mutagenesis. The thus obtained plasmid is pMOG180.

EXAMPLE 5

Cloning of cDNA's corresponding with osmotin and preparation ofthe binary vector pMOG404

A tobacco cDNA library was made using a ZAP-cDNA synthesis kit (Stratagene Cat #200400,200401). From TMV-infected Samsun NN tobacco leaves, polyadenylated RNA was isolated and used for the synthesis of cDNA, using standard techniques known to researchers in this field. After treatment with EcoRI and XhoI, the cDNA fragments were ligated to the compatible termini of the lambda ZAP arms.

The above described lambda ZAP tobacco cDNA library was screened with a DNA probe for sequences that are homologous to the NP24 gene of tomato (King et al., (1988), Plant. Mol. Biol. 10, 401–412). With the aid of the plaque hybridisation technique from Benton and Davis (1977, Science 196, 180–182) approximately 7 recombinant phages were identified. The inserts in the DNA of these phages were subcloned in a pBluescript (SK-) plasmid, using the in vivo excision method. The nucleotide sequence of the different cDNA clones was determined using the M13 sequence method. These analyses in combination with comparisons of the partial amino-acid sequence of the AP20 protein showed that only 3 clones contained a nearly complete cDNA sequence. One cDNA clone contains the complete coding sequence for osmotin, except for the Adenine-Thymidine dinucleotide of the translation initiation codon (Singh et al., 1989, supra). This clone is further designated as osmotin cDNA clone. The N-terminal amino-acid sequence of the characterised AP20 protein matches exactly the corresponding sequence of osmotin as deduced from the osmotin cDNA clone.

With the use of PCR a BamHI recognition site and an Adenine-Thymidine dinucleotide is introduced in front of the osmotin cDNA, hence creating a translation initiation codon; behind the gene a BamHI recognition site was introduced. For these PCR reactions the cligonucleotides SEQID 2 and SEQID3 were used as primers; (see Sequence Protocol) SEQID2 and SEQID 3. The modified cDNA sequence is verified for undesirable mutations that can occur as a consequence of the PCR method. The sequence is shown in the Sequence Protocol, as SEQID 4. The osmotin gene was cloned as a BamHI fragment into the BamHI linearised vector pMOG180 (see Example VIII for the construction; FIG. 2). The obtained expression construct contains on a SstI-HindIII fragment the cauliflower mosaic virus (CaMV) 35S promoter in front of the osmotin gene which in its turn is followed by the nopaline synthase (nos) transcription terminator. The expression construct was cloned into the binary vector pMOG23 (deposited at the Centraal Bureau voor Schimmelcultures te Baarn, The Netherlands, No. CBS 102.90), after linearisation with the restriction enzymes SstI and HindIII. The obtained plasmid pMOG404 (FIG. 3) now contains both the osmotin gene, as well as the NPTII gene localised between the left and right T-DNA border sequences. With the aid of the plasmid pRK2013, this binary vector was mobilised from *E. coli* DH5α to the *Agrobacterium tumefaciens* strain LBA4404. The transconjugant LBA4404 (pMOG404) was isolated from this crossing on selection medium containing 20 mg/l rifampicin and 100 mg/l kanamycine.

EXAMPLE 6

Construction of pMOG405 encoding an extracellular osmotin

Wild-type osmotin has been reported to occur intracellularly, predominantly in vacuoles of plant cells (Singh et al., 1987, supra). To provide for secretion of osmotin into the extracel.lular space, a translational stop-codon is introduced into the wild-type osmotin CDNA as present in pMOG404, between codon 20 and 21 as numbered from the C-terminal end of the protein encoded by the cDNA. Using the PCR technique known to those skilled in the art the stop-codon is created by the insertion of a thymidine (T) residue between nucleotide 694 and 695 with respect to the sequence presented as SEQID 4 in the sequence protocol. The hence modified osmotin sequence is checked for undesired mutations that might occur as a consequence of the PCR methodology. The mutated cDNA encodes an osmotin lacking the 20 C-terminal amino-acids of the primary translation product of wild-type osmotin mRNA. The binary vector thus obtained was called pMOG405 and the corresponding Agrobacterium transconjugant LBA4404 (pMOG405). As shown in EXAMPLE 8 the osmotin encoded by pMOG405 is indeed targetted extracellularly.

EXAMPLE 7

Preparation of transgenic plants

The transformation of potato (Solanum tuberosum cv. Bintje) with Agrobacterium strains LBA4404 (pMOG404) and LBA4404 (pMOG405) is performed according to the procedure described by Hoekema et 1., (1989), Bio/Technology 7, 273–278.

For the transformation of tobacco use is made of the leaf-disc dip method (Ho:rsch et al., (1985), Science 227 1229–1231). Leaf-discs were cocultivated with Aqrobacterium strains LBA4404 (pMOG404) or LBA4404 (pMOG405) and subsequently grown on selection medium with 100 mg/ml kanamycine, using standard methods. The transgenic shoots were regenerated into whole plants and analysed for expression of the osmotin gene. For this analysis use was made of the so-called Western blotting technique, using antibodies raised against pathogenesis-related protein PR-S, and the Northern blotting technique using an osmotin cDNA fragment as probe. The Western blot analysis revealed no difference in size between osmotin encoded by pMOG404 and osmotin encoded by pMOG405, although the osmotin coding regions in the two constructs differ twenty codons in length. This result suggests that in the plant wild-type osmotin is C-terminally processed.

EXAMPLE 8

Analysis of pMOG404 and pMOG405-transgenic tobacco plants for targetting of the transgene-Product.

To show extracellular targetting of osmotin in pMOG405-transgenic tobacco plants, the following experiment was carried out. Leaves of Fl plants from pMOG404-transgenic plant lines and from pMOG405-transgenic plant lines expressing the newly introduced osmotin gene, and leaves of non-transgenic plants were used for the extraction of total proteins and of extracellular proteins. For the extraction of extracellular proteins extracellular fluid was collected according to the procedure described by De Wit and Spikman (1982, Physiol. Plant Pathol. 20, 1–11). After the isolation of the extracellular fluid, proteins were extracted as well from the remaining leaf material. For the analysis of proteins in total extracts (Total), in the extracellular fluid (EF) and in extracts of leaves from which the extracellular fluid was removed (-EF), use was made of the so-called Western blotting technique, using AP20 specific antibodies, or antibodies raised against pathogenesis-related protein PR-S. The results shown in Table 1 indicate that with the pMOG405-transgenic plants osmotin is indeed properly targetted into the extracellular space.

TABLE 1

Targetting of osmotin into the extracellular space in pMOG405-transgenic tobacco plants.

| Plant | Protein sample | | |
|---|---|---|---|
| | Total | EF | -EF |
| non-transgenic | – | – | – |
| pMOG404 | ++++ | – | ++++ |
| pMOG405 | ++++ | +++ | + |

–: no AP20; + to ++++: increasing amount of osmotin

EXAMPLE 9

Analysis for fungal resistance in transgenic tobacco plants

The fungus *Phytophthora nicotianae* var. nicotianae (Pnn) is an Oomycete. It is a root-pathogen with, inter alia, tobacco as a host. Infection of the plant results in wilting of the leaves and/or rot of the base of the stem (black shank). Eventually, the tobacco plant dies from the infection.

Leaf discs with a diameter of about one to two centimeter were obtained from pMOG404-transgenic, vector-transgenic and non-transgenic tobacco plants. Leaf-discs were floated upside down in Petridishes containing sterile water. Onto each disc 10 µl of a zoospore suspension (5000 sp/ml) was pipetted. In each experiment 3 times 10 discs were used, i.e. in total 20 control discs per experiment. After approximately one day, the first signs of a starting infection were visible cn the control discs. After three days the control leaf-discs were entirely affected (water-soaking). The leaf-discs derived from pMOG404-transgenic plants did show less symptoms after three days. The results of the experiment could be reproduced several times.

This example suggests that tobacco plants constitutively expressing an intracellular osmotin gene show reduced susceptibility to the fungus *Phytophthora nicotianae* var. nicotianae (Pnn), a natural pathogen of tobacco plants.

To assess the fungal resistance to *P. nicotianae* var. nicotianae of whole tobacco plants, the following experiment can be performed. Ten transgenic plants transformed with LBA4404 (pMOG404) (good expressors of the osmotin gene are selected), ten transgenic plants transformed with the vector not containing the osmotin gene (designated as vector-transgenic plants) and ten non-transformed plants are inoculated with a suspension containing $2 \times 10^5$ Pnn zoospores in water. This suspension is pipetted at the basis of the stem onto the soil. Thereafter 100 ml water is poured at the stem base. Subsecuently, the development of disease symptoms is monitored in time. After two to three days the control plants (non-transgenic and vector-transgenic plants) show the first symptoms of disease; i.e. wilting. Of the pMOG404-transgenic plants some show a slight delay in the development of the disease symptoms. However, a better protection is desired. The effect of the localisation of osmotin in the plant will be evaluated in the following experiment.

EXAMPLE 10

Analysis for fungal resistance in transgenic tobacco plants that express an extracellularly targetted osmotin With the aid of Agrobacterium tumefaciens LBA4404 (pMOG405) transgenic tobacco plants were obtained, that express the altered osmotin gene, eventually resulting in apoplast-targetting of the produced osmotin. Good expressors of the gene encoding extracellularly targetted osmotin, for analysis see EXAMPLE 8, were analysed for resistance to *Phytophthora nicotianae* var. nicotianae (Pnn).

The experiments were performed on 10 leaf-discs obtained from one pMOG404-transgenic, two pMOG405-transgenic lines, and one non-transgenic tobacco line. After three days, the results of the non-transgenic plant (line #2), a good expresser of pMOG404 line #1, and two good expressors of pMOG405 (lines #6 and #9) are analysed. The results are given in Table 2.

TABLE 2

Fungal resistance assay on leaf-discs obtained from transgenic and non-trangenic tobacco lines tested on Phytophthora nicotianae

| Plant line | Area Infected |
| --- | --- |
| #2 | 8 discs 100% |
|  | 2 discs 60% |
| pMOG404 #1 | 7 discs 100% |
|  | 3 discs < 25% |
| pMOG405 #6 | 1 disc 100% |
|  | 2 discs 60% |
|  | 7 discs < 25% |
| pMOG405 #9 | 3 discs 100% |
|  | 2 discs 60% |
|  | 5 discs < 25% |

Percentages express area affected by *P. nicotianae* infection after 3 days.

The results from Table 2 clearly show an enhanced antifungal effect in leaf-discs if osmotin is targetted to the extracellular space, as compared to the intracellularly localised osmotin. We predict that the fungal resistance as shown here in leaf-discs is reflected in whole plants as well.

To assess the fungal resistance in planta the lines mentioned above can be tested for fungal resistance as described in the previous EXAMPLE. We predict that pMOG405-transgenic tobacco plants show considerably better resistance compared to the lines obtained after transformation with pMOG404.

From the observations on the antifungal effect of osmotin-like proteins, we conclude that an antifungal effect can be obtained if an antifungal protein is expressed in a plant at high level, such as illustrated here under the control of CaMV 35S, i.e. a constitutive promoter.

Moreover, it is found that when synthesis of an intracellular antifungal protein is accompanied by extracellular targetting a significant enhancement of the antifungal effect is obtained. Recent results obtained from similar tests with chitinases and β-1,3-glucanases confirm this finding in toto. Most importantly, the finding that osmotin-like proteins, which are intracellular proteins, show an antifungal effect, completes a picture that is becoming increasingly clear, as is explained below.

It has been known for some time that some chitinases and glucanases exhibit an antifungal effect. The antifungal effect of at least some plant chitinases and glucanases in planta (i.e. in transformed plants) has been difficult to establish. The reason for this is now clear, for very recent findings strongly suggest that only the specimens of the said enzymes that occur intracellularly have the mentioned antifungal effect. This is now confirmed by a third group of antifungal proteins, i.e. osmotin-like proteins, which are intracellular proteins, whereas PR-S, which is very homologous to osmotin-like proteins and produced upon induction of resistance, but which is an extracellular protein, has no antifungal effect whatsoever. A fourth category of so-called pathogenesis-related proteins (chitinases, glucanases and osmotin-like proteins being the other three groups), the PR-1 proteins, also fit in this picture.

However, if no measures are taken, expression of the genes encoding intracellular antifungal proteins in plants transformed with the said genes, probably only causes a very modest antifungal effect, because these proteins do not reach their preferred site of action.

From these observations we conclude the following:

1) Of all the proteins that are produced upon induction of resistance, including at least the chitinases, the glucanases and the osmotin-like proteins, the intracellular forms will show a significantly higher antifungal effect than their extracellular counterparts. Putatively the extracellular forms of most if not all classes of PR-proteins will show little or no antifungal effect at all.

2) As our experiments with the pMOG405 plants have pointed out, the preferred site of action of an antifungal protein, irrespective of its authentic localisation in the plant, is the extracellular space.

3) To effectively combat fungal attack the use of intracellular proteins which are produced upon induction of resistance in an antifungal preparation is highly recommended.

4) Setting out to obtain plants with reduced susceptibility to fungi, said plants are to be transformed with an open reading frame encoding an intracellular antifungal protein which upon production is targetted to its preferred site of action, which is the extracellular space.

However, from what is stated above, it is not to be understood that literally all intracellular proteins that are produced upon induction of the hypersensitive response indeed have an antifungal effect. For this reason, the 'inverted approach', i.e. starting from an antifungal effect rather than from an enzymatic effect, is very useful to sort out only those (intracellular) proteins that actually have an antifungal effect. Then, the effect on fungal resistance of these proteins is to be tested in planta, by transformation of a susceptible plant with an open reading frame, encoding the said antifungal protein, preferably after modification of the open reading frame to provide for extracellular targetting.

EXAMPLE 11

Analysis of fungal resistance in transgenic potato plants

To test the susceptibility of potato plants transformed with pMOG404 and pMOG405, 20 of the best transgenic osmotin expressors are sprayed with a suspension of $1 \times 10^5$ spores of the fungus *Phytophthora infestans* until wet. *P. infestans* is a formidable pathogen of the potato plant. It causes complete wilting of the leaves, affection of the stem and eventually death of the plant. As a control 20 non-transformed plants and 20 plants transformed with the vector without the osmotin gene (vector-transgenic) are sprayed with an equal amount of spores. The plants are grown in a growth room at 18° C. and air humidity of 95–100%. The progress of the disease is evaluated at day 7 and day 14 after spraying, by determining the leaf area that is affected by the fungus. The quantity of affected leaf area is expressed as a percentage of the total leaf area of all the counted leaves. Per plant 8 to 10 (lower) leaves are counted; an average is calculated of the results of all the counted leaves of each plant. In the Table below estimations are given of the results. (+0–25% of total leaf area affected; ++25–50% affected; +++50–75% affected; ++++75–100% affected).

TABLE 3

Estimated results of susceptibility of potato plants against the fungus *P. infestans*

|  | + | ++ | +++ | ++++ |
|---|---|---|---|---|
| day 7 | | | | |
| non-transgenic | – | – | 15% ± 10% | 85% ± 10% |
| vector-transgenic | – | – | 15 ± 10% | 85% ± 10% |
| pMOG404-transgenic | 25% ± 10% | 25% ± 10% | 20% ± 10% | 30% ± 10% |
| pMOG405-transgenic | 25% ± 10% | 30% ± 10% | 30% ± 10% | 15% ± 10% |
| day 14 | | | | |
| non-transgenic | | | 10% ± 10% | 90% ± 10% |
| vector-transgenic | | | 10% ± 10% | 90% ± 10% |

TABLE 3-continued

Estimated results of susceptibility of potato plants against the fungus *P. infestans*

|  | + | ++ | +++ | ++++ |
|---|---|---|---|---|
| pMOG404-transgenic | 20% ± 10% | 10% ± 10% | 10% ± 10% | 60% ± 10% |
| pMOG405-transgenic | 20% ± 10% | 25% ± 10% | 30% ± 10% | 25% ± 10% |

With the inocula used here, the non-transformed and vector transformed plants are almost completely affected at day 7. From the pMOG404 plants at day 7, only about 30% of the plants will be severely affected; about 70% of the pMOG404 plants will show clearly delayed disease development (+to +++) as compared to the control plants. It is expected that at day 14 approximately 10–50% of the pMOG404 plants will only show light to moderate (+to ++) symptoms of infection, while even 10–30% will only be slightly affected or not affected at all (+). The extracellularly targetted osmotin (i.e. the pMOG405 plants) will even show a more delayed development of the disease than the pMOG404-transgenic lines.

We claim:

1. A method for inhibiting the growth and/or germination of a fungus that is susceptible to an osmotin protein by contacting the fungus, or causing the fungus to be contacted, with an effective amount of the osmotin protein.

2. A method according to claim 1, wherein the fungus is a plant pathogenic fungus.

3. A method according to claim 2, wherein the fungus is an Oomycete.

4. A method according to claim 3, wherein the fungus is selected from the genus Phytophthora.

5. A method according to claim 4, wherein the fungus is selected from the genus *Phytophthora infestans* or *Phytophthora nicotianae.*

6. A method according to claim 1, wherein the osmotin protein is derived from a plant selected from a group consisting of alfalfa, bean, carrot, cotton, millet, potato, soybean, tobacco and tomato.

7. A method according to claim 6, wherein the osmotin protein is derived from tobacco or tomato.

8. A method according to claim 7, wherein the osmotin protein comprises the amino acid sequence depicted in SEQ ID NO: 6 or 7.

9. A method according to claim 1, wherein the effective amount of the protein is produced by an organism having incorporated into its genome a chimeric gene comprising a) an open reading frame encoding the osmotin protein, or a precursor of the osmotin protein, and having operably linked thereto b) a regulatory region which causes the chimeric gene to be expressed in said organism.

10. A method according to claim 9, wherein said organism is a plant.

11. A method according to claim 10, wherein said plant is a monocotyledonous plant.

12. A method according to claim 10, wherein said plant is selected from the dicotyledoneae.

13. A method according to claim 12, wherein said plant is selected from the group consisting of tobacco and potato.

14. A method according to claim 9, wherein the regulatory region comprises a transcriptional initiation region of the gene encoding the 35S RNA of CaMV.

15. A method according to claim 9, wherein the open reading frame encodes a precursor of osmotin protein having the amino acid sequence depicted in SEQ ID NO: 6 or 7.

16. A method according to claim 10, wherein the open reading frame has a nucleotide sequence encoding the amino acid sequence of SEQ ID NO:6 or 7.

17. A method according to claim 2, wherein hyphae or spores of said fungus are in contact with a plant.

18. A method as claimed in claim 1 wherein the osmotin protein contacts, or is caused to contact, spores of the fungus.

19. A method for protecting a plant against disease caused by infection of the plant by a fungus, said method comprising transforming the plant with a chimeric gene comprising an open reading encoding an osmotin protein or a precursor of an osmotin protein and having operably linked thereto a regulatory region which causes the chimeric gene to be expressed in an amount effective to protect the plant against the disease.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 34
        ( B ) TYPE: Nucleotide
        ( C ) STRANDEDNESS: Double
        ( D ) TOPOLOGY: Linear ( i i ) MOLECULE TYPE: Synthetic ( v i ) ORIGINAL SOURCE:
        ( A ) ORGANISM: Alfalfa Mosaic Virus ( x i ) SEQUENCE DESCRIPTION: SEQ ID NO:1:

TTTTTATTTT TAATTTTCTT TCAAATACTT CCAG     3 4

( 2 ) INFORMATION FOR SEQ ID NO:2:

( i ) SEQUENCE CHARACTERISTICS:
        ( A ) LENGTH: 32
        ( B ) TYPE: Nucleotide
        ( C ) STRANDEDNESS: Single
        ( D ) TOPOLOGY: Linear ( i i ) MOLECULE TYPE: Synthetic ( x i ) SEQUENCE DESCRIPTION: SEQ ID NO:2:

GCCGGATCCA ATTCGGCACA TGGGCAACTT GA     3 2

( 2 ) INFORMATION FOR SEQ ID NO:3:

( i ) SEQUENCE CHARACTERISTICS:
        ( A ) LENGTH: 26
        ( B ) TYPE: Nucleotide
        ( C ) STRANDEDNESS: Single
        ( D ) TOPOLOGY: Linear ( i i ) MOLECULE TYPE: Synthetic ( x i ) SEQUENCE DESCRIPTION: SEQ ID NO:3:

```
GTTTATTACA GCAAGGATCC TGACTT                                          26
```

( 2 ) INFORMATION FOR SEQ ID NO:4:

( i ) SEQUENCE CHARACTERISTICS:
        ( A ) LENGTH: 883
        ( B ) TYPE: Nucleotide
        ( C ) STRANDEDNESS: Double
        ( D ) TOPOLOGY: Linear ( i i ) MOLECULE TYPE: cDNA ( v i ) ORIGINAL SOURCE:
        ( A ) ORGANISM: Nicotiana tabacum ( x i ) SEQUENCE DESCRIPTION: SEQ ID NO:4:

```
GGATCCAATT CGGCAC                                                         16

ATG GGC AAC TTG AGA TCT TCT TTT GTT TTC TTC CTC CTT GCC                   58
Met Gly Asn Leu Arg Ser Ser Phe Val Phe Phe Leu Leu Ala
                  5                  10

TTG GTG ACT TAT ACT TAT GCT GCC ACT ATC GAG GTC CGA AAC                  100
Leu Val Thr Tyr Thr Tyr Ala Ala Thr Ile Glu Val Arg Asn
 15              20                  25

AAC TGT CCG TAC ACC GTT TGG GCG GCG TCG ACA CCC ATA GGC                  142
Asn Cys Pro Tyr Thr Val Trp Ala Ala Ser Thr Pro Ile Gly
     30              35              40

GGT GGC CGG CGT CTC GAT CGA GGC CAA ACT TGG GTG ATC AAT                  184
Gly Gly Arg Arg Leu Asp Arg Gly Gln Thr Trp Val Ile Asn
         45              50              55

GCG CCA CGA GGT ACT AAA ATG GCA CGT GTA TGG GGC CGT ACT                  226
Ala Pro Arg Gly Thr Lys Met Ala Arg Val Trp Gly Arg Thr
             60              65                  70

AAT TGT AAC TTC AAT GCT GCT GGT AGG GGT ACG TGC CAA ACC                  268
Asn Cys Asn Phe Asn Ala Ala Gly Arg Gly Thr Cys Gln Thr
                 75              80

GGT GAC TGT GGT GGA GTC CTA CAG TGC ACC GGG TGG GGT AAA                  310
Gly Asp Cys Gly Gly Val Leu Gln Cys Thr Gly Trp Gly Lys
 85              90                  95

CCA CCA AAC ACC TTG GCT GAA TAC GCT TTG GAC CAA TTC AGT                  352
Pro Pro Asn Thr Leu Ala Glu Tyr Ala Leu Asp Gln Phe Ser
100             105                  110

GGT TTA GAT TTC TGG GAC ATT TCT TTA GTT GAT GGA TTC AAC                  394
Gly Leu Asp Phe Trp Asp Ile Ser Leu Val Asp Gly Phe Asn
        115              120                 125

ATT CCG ATG ACT TTC GCC CCG ACT AAC CCT AGT GGA GGG AAA                  436
Ile Pro Met Thr Phe Ala Pro Thr Asn Pro Ser Gly Gly Lys
            130              135                 140

TGC CAT GCA ATT CAT TGT ACG GCT AAT ATA AAC GGC GAA TGT                  478
Cys His Ala Ile His Cys Thr Ala Asn Ile Asn Gly Glu Cys
                145                  150

CCC CGC GAA CTT AGG GTT CCC GGA GGA TGT AAT AAC CCT TGT                  520
Pro Arg Glu Leu Arg Val Pro Gly Gly Cys Asn Asn Pro Cys
155             160                  165
```

| | | | | | | | | | | | | | | |
|---|---|---|---|---|---|---|---|---|---|---|---|---|---|---|
| ACT | ACA | TTC | GGA | GGA | CAA | CAA | TAT | TGT | TGC | ACA | CAA | GGA | CCT | 562 |
| Thr | Thr | Phe | Gly | Gly | Gln | Gln | Tyr | Cys | Cys | Thr | Gln | Gly | Pro | |
| | 170 | | | | 175 | | | | | 180 | | | | |
| TGT | GGT | CCT | ACA | TTT | TTC | TCA | AAA | TTT | TTC | AAA | CAA | AGA | TGC | 604 |
| Cys | Gly | Pro | Thr | Phe | Phe | Ser | Lys | Phe | Phe | Lys | Gln | Arg | Cys | |
| | | 185 | | | | | 190 | | | | | 195 | | |
| CCT | GAT | GCC | TAT | AGC | TAC | CCA | CAA | GAT | GAT | CCT | ACT | AGC | ACT | 646 |
| Pro | Asp | Ala | Tyr | Ser | Tyr | Pro | Gln | Asp | Asp | Pro | Thr | Ser | Thr | |
| | | | 200 | | | | 205 | | | | | | 210 | |
| TTT | ACT | TGC | CCT | GGT | GGT | AGT | ACA | AAT | TAT | AGG | GTT | ATC | TTT | 688 |
| Phe | Thr | Cys | Pro | Gly | Gly | Ser | Thr | Asn | Tyr | Arg | Val | Ile | Phe | |
| | | | | 215 | | | | | 220 | | | | | |
| TGT | CCT | AAT | GGT | CAA | GCT | CAC | CCA | AAT | TTT | CCC | TTG | GAA | ATG | 730 |
| Cys | Pro | Asn | Gly | Gln | Ala | His | Pro | Asn | Phe | Pro | Leu | Glu | Met | |
| 225 | | | | | 230 | | | | | 235 | | | | |
| CCT | GGA | AGT | GAT | GAA | GTG | GCT | AAG | TAG | AGTGGCTATT | | | | | 767 |
| Pro | Gly | Ser | Asp | Glu | Val | Ala | Lys | | | | | | | |
| | 240 | | | | | 245 | | | | | | | | |

| | | | | | |
|---|---|---|---|---|---|
| TCTGTAATAA | GATCACCTTT | TGGTCAAATT | ATTCTATCGA | CACGTTAGTG | 817 |
| TAAGACAATC | TATTTGACTC | GTTTTTATAG | TTACGTACTT | TGTTTGAAGT | 867 |
| GATCAAGTCA | GGATCC | | | | 883 |

( 2 ) INFORMATION FOR SEQ ID NO:5:

( i ) SEQUENCE CHARACTERISTICS:
        ( A ) LENGTH: 884
        ( B ) TYPE: Nucleotide
        ( C ) STRANDEDNESS: Double
        ( D ) TOPOLOGY: Linear ( i i ) MOLECULE TYPE: cDNA ( v i ) ORIGINAL SOURCE:
        ( A ) ORGANISM: Nicotiana tabacum ( x i ) SEQUENCE DESCRIPTION: SEQ ID NO:5:

| | | | | | | | | | | | | | | |
|---|---|---|---|---|---|---|---|---|---|---|---|---|---|---|
| GGATCCAATT | CGGCAC | | | | | | | | | | | | | 16 |
| ATG | GGC | AAC | TTG | AGA | TCT | TCT | TTT | GTT | TTC | TTC | CTC | CTT | GCC | 58 |
| Met | Gly | Asn | Leu | Arg | Ser | Ser | Phe | Val | Phe | Phe | Leu | Leu | Ala | |
| | | | | 5 | | | | | 10 | | | | | |
| TTG | GTG | ACT | TAT | ACT | TAT | GCT | GCC | ACT | ATC | GAG | GTC | CGA | AAC | 100 |
| Leu | Val | Thr | Tyr | Thr | Tyr | Ala | Ala | Thr | Ile | Glu | Val | Arg | Asn | |
| 15 | | | | | 20 | | | | 25 | | | | | |
| AAC | TGT | CCG | TAC | ACC | GTT | TGG | GCG | GCG | TCG | ACA | CCC | ATA | GGC | 142 |
| Asn | Cys | Pro | Tyr | Thr | Val | Trp | Ala | Ala | Ser | Thr | Pro | Ile | Gly | |
| | 30 | | | | | 35 | | | | 40 | | | | |
| GGT | GGC | CGG | CGT | CTC | GAT | CGA | GGC | CAA | ACT | TGG | GTG | ATC | AAT | 184 |
| Gly | Gly | Arg | Arg | Leu | Asp | Arg | Gly | Gln | Thr | Trp | Val | Ile | Asn | |
| | | 45 | | | | | 50 | | | | | 55 | | |
| GCG | CCA | CGA | GGT | ACT | AAA | ATG | GCA | CGT | GTA | TGG | GGC | CGT | ACT | 226 |
| Ala | Pro | Arg | Gly | Thr | Lys | Met | Ala | Arg | Val | Trp | Gly | Arg | Thr | |
| | | | 60 | | | | 65 | | | | | 70 | | |
| AAT | TGT | AAC | TTC | AAT | GCT | GCT | GGT | AGG | GGT | ACG | TGC | CAA | ACC | 268 |
| Asn | Cys | Asn | Phe | Asn | Ala | Ala | Gly | Arg | Gly | Thr | Cys | Gln | Thr | |
| | | | | 75 | | | | | 80 | | | | | |
| GGT | GAC | TGT | GGT | GGA | GTC | CTA | CAG | TGC | ACC | GGG | TGG | GGT | AAA | 310 |
| Gly | Asp | Cys | Gly | Gly | Val | Leu | Gln | Cys | Thr | Gly | Trp | Gly | Lys | |
| 85 | | | | | 90 | | | | | 95 | | | | |
| CCA | CCA | AAC | ACC | TTG | GCT | GAA | TAC | GCT | TTG | GAC | CAA | TTC | AGT | 352 |
| Pro | Pro | Asn | Thr | Leu | Ala | Glu | Tyr | Ala | Leu | Asp | Gln | Phe | Ser | |
| | 100 | | | | | 105 | | | | | 110 | | | |

|     |     |     |     |     |     |     |     |     |     |     |     |     |     |
| --- | --- | --- | --- | --- | --- | --- | --- | --- | --- | --- | --- | --- | --- |
| GGT | TTA | GAT | TTC | TGG | GAC | ATT | TCT | TTA | GTT | GAT | GGA | TTC | AAC |
| Gly | Leu | Asp | Phe | Trp | Asp | Ile | Ser | Leu | Val | Asp | Gly | Phe | Asn |
|     | 115 |     |     |     |     | 120 |     |     |     |     |     | 125 |     |

394

|     |     |     |     |     |     |     |     |     |     |     |     |     |     |
| --- | --- | --- | --- | --- | --- | --- | --- | --- | --- | --- | --- | --- | --- |
| ATT | CCG | ATG | ACT | TTC | GCC | CCG | ACT | AAC | CCT | AGT | GGA | GGG | AAA |
| Ile | Pro | Met | Thr | Phe | Ala | Pro | Thr | Asn | Pro | Ser | Gly | Gly | Lys |
|     |     |     | 130 |     |     |     |     | 135 |     |     |     |     | 140 |

436

|     |     |     |     |     |     |     |     |     |     |     |     |     |     |
| --- | --- | --- | --- | --- | --- | --- | --- | --- | --- | --- | --- | --- | --- |
| TGC | CAT | GCA | ATT | CAT | TGT | ACG | GCT | AAT | ATA | AAC | GGC | GAA | TGT |
| Cys | His | Ala | Ile | His | Cys | Thr | Ala | Asn | Ile | Asn | Gly | Glu | Cys |
|     |     |     |     | 145 |     |     |     |     | 150 |     |     |     |     |

478

|     |     |     |     |     |     |     |     |     |     |     |     |     |     |
| --- | --- | --- | --- | --- | --- | --- | --- | --- | --- | --- | --- | --- | --- |
| CCC | CGC | GAA | CTT | AGG | GTT | CCC | GGA | GGA | TGT | AAT | AAC | CCT | TGT |
| Pro | Arg | Glu | Leu | Arg | Val | Pro | Gly | Gly | Cys | Asn | Asn | Pro | Cys |
| 155 |     |     |     |     | 160 |     |     |     |     | 165 |     |     |     |

520

|     |     |     |     |     |     |     |     |     |     |     |     |     |     |
| --- | --- | --- | --- | --- | --- | --- | --- | --- | --- | --- | --- | --- | --- |
| ACT | ACA | TTC | GGA | GGA | CAA | CAA | TAT | TGT | TGC | ACA | CAA | GGA | CCT |
| Thr | Thr | Phe | Gly | Gly | Gln | Gln | Tyr | Cys | Cys | Thr | Gln | Gly | Pro |
|     | 170 |     |     |     |     | 175 |     |     |     |     | 180 |     |     |

562

|     |     |     |     |     |     |     |     |     |     |     |     |     |     |
| --- | --- | --- | --- | --- | --- | --- | --- | --- | --- | --- | --- | --- | --- |
| TGT | GGT | CCT | ACA | TTT | TTC | TCA | AAA | TTT | TTC | AAA | CAA | AGA | TGC |
| Cys | Gly | Pro | Thr | Phe | Phe | Ser | Lys | Phe | Phe | Lys | Gln | Arg | Cys |
|     |     | 185 |     |     |     |     | 190 |     |     |     |     | 195 |     |

604

|     |     |     |     |     |     |     |     |     |     |     |     |     |     |
| --- | --- | --- | --- | --- | --- | --- | --- | --- | --- | --- | --- | --- | --- |
| CCT | GAT | GCC | TAT | AGC | TAC | CCA | CAA | GAT | GAT | CCT | ACT | AGC | ACT |
| Pro | Asp | Ala | Tyr | Ser | Tyr | Pro | Gln | Asp | Asp | Pro | Thr | Ser | Thr |
|     |     |     | 200 |     |     |     | 205 |     |     |     |     | 210 |     |

646

|     |     |     |     |     |     |     |     |     |     |     |     |     |     |
| --- | --- | --- | --- | --- | --- | --- | --- | --- | --- | --- | --- | --- | --- |
| TTT | ACT | TGC | CCT | GGT | GGT | AGT | ACA | AAT | TAT | AGG | GTT | ATC | TTT |
| Phe | Thr | Cys | Pro | Gly | Gly | Ser | Thr | Asn | Tyr | Arg | Val | Ile | Phe |
|     |     |     |     | 215 |     |     |     |     | 220 |     |     |     |     |

688

|     |     |
| --- | --- |
| TGT | CCT |
| Cys | Pro |
| 225 |     |

694

| | |
|---|---|
| TAATGGTCAA GCTCACCCAA ATTTTCCCTT GGAAATGCCT GGAAGTGATG | 744 |
| AAGTGGCTAA GTAGAGTGGC TATTTCTGTA ATAAGATCAC CTTTTGGTCA | 794 |
| AATTATTCTA TCGACACGTT AGTGTAAGAC AATCTATTTG ACTCGTTTTT | 844 |
| ATAGTTACGT ACTTGTTTG AAGTGATCAA GTCAGGATCC | 884 |

( 2 ) INFORMATION FOR SEQ ID NO: 6:

( i ) SEQUENCE CHARACTERISTICS:
        ( A ) LENGTH: 246 Amino Acids
        ( B ) TYPE: Amino Acid
        ( D ) TOPOLOGY: Linear ( x i ) SEQUENCE DESCRIPTION: SEQ ID NO: 6:

|     |     |     |     |     |     |     |     |     |     |     |     |
| --- | --- | --- | --- | --- | --- | --- | --- | --- | --- | --- | --- |
| Met | Gly | Asn | Leu | Arg | Ser | Ser | Phe | Val | Phe | Leu | Leu | Ala |
|     |     |     |     | 5   |     |     |     |     | 10  |     |     |     |

| | | | | | | | | | | | |
| --- | --- | --- | --- | --- | --- | --- | --- | --- | --- | --- | --- |
| Leu | Val | Thr | Tyr | Thr | Tyr | Ala | Ala | Thr | Ile | Glu | Val | Arg | Asn |
| 15  |     |     |     |     | 20  |     |     |     |     | 25  |     |     |     |

| | | | | | | | | | | | |
| --- | --- | --- | --- | --- | --- | --- | --- | --- | --- | --- | --- |
| Asn | Cys | Pro | Tyr | Thr | Val | Trp | Ala | Ala | Ser | Thr | Pro | Ile | Gly |
|     | 30  |     |     |     |     | 35  |     |     |     |     | 40  |     |     |

| | | | | | | | | | | | |
| --- | --- | --- | --- | --- | --- | --- | --- | --- | --- | --- | --- |
| Gly | Gly | Arg | Arg | Leu | Asp | Arg | Gly | Gln | Thr | Trp | Val | Ile | Asn |
|     |     |     | 45  |     |     |     |     | 50  |     |     |     |     | 55  |

| | | | | | | | | | | | |
| --- | --- | --- | --- | --- | --- | --- | --- | --- | --- | --- | --- |
| Ala | Pro | Arg | Gly | Thr | Lys | Met | Ala | Arg | Val | Trp | Gly | Arg | Thr |
|     |     |     |     | 60  |     |     |     |     | 65  |     |     |     | 70  |

| | | | | | | | | | | | |
| --- | --- | --- | --- | --- | --- | --- | --- | --- | --- | --- | --- |
| Asn | Cys | Asn | Phe | Asn | Ala | Ala | Gly | Arg | Gly | Thr | Cys | Gln | Thr |
|     |     |     |     | 75  |     |     |     |     | 80  |     |     |     |     |

| | | | | | | | | | | | |
| --- | --- | --- | --- | --- | --- | --- | --- | --- | --- | --- | --- |
| Gly | Asp | Cys | Gly | Gly | Val | Leu | Gln | Cys | Thr | Gly | Trp | Gly | Lys |
| 85  |     |     |     |     | 90  |     |     |     |     | 95  |     |     |     |

| | | | | | | | | | | | |
| --- | --- | --- | --- | --- | --- | --- | --- | --- | --- | --- | --- |
| Pro | Pro | Asn | Thr | Leu | Ala | Glu | Tyr | Ala | Leu | Asp | Gln | Phe | Ser |
|     |     |     | 100 |     |     |     | 105 |     |     |     |     | 110 |     |

| | | | | | | | | | | | |
| --- | --- | --- | --- | --- | --- | --- | --- | --- | --- | --- | --- |
| Gly | Leu | Asp | Phe | Trp | Asp | Ile | Ser | Leu | Val | Asp | Gly | Phe | Asn |
|     |     |     | 115 |     |     |     |     | 120 |     |     |     |     | 125 |

```
Ile  Pro  Met  Thr  Phe  Ala  Pro  Thr  Asn  Pro  Ser  Gly  Gly  Lys
               130                      135                       140

Cys  His  Ala  Ile  His  Cys  Thr  Ala  Asn  Ile  Asn  Gly  Glu  Cys
                    145                      150

Pro  Arg  Glu  Leu  Arg  Val  Pro  Gly  Gly  Cys  Asn  Asn  Pro  Cys
155                      160                      165

Thr  Thr  Phe  Gly  Gly  Gln  Gln  Tyr  Cys  Cys  Thr  Gln  Gly  Pro
     170                      175                           180

Cys  Gly  Pro  Thr  Phe  Phe  Ser  Lys  Phe  Phe  Lys  Gln  Arg  Cys
          185                      190                          195

Pro  Asp  Ala  Tyr  Ser  Tyr  Pro  Gln  Asp  Asp  Pro  Thr  Ser  Thr
               200                      205                       210

Phe  Thr  Cys  Pro  Gly  Gly  Ser  Thr  Asn  Tyr  Arg  Val  Ile  Phe
                    215                      220

Cys  Pro  Asn  Gly  Gln  Ala  His  Pro  Asn  Phe  Pro  Leu  Glu  Met
225                      230                      235

Pro  Gly  Ser  Asp  Glu  Val  Ala  Lys
     240                      245
```

(2) INFORMATION FOR SEQ ID NO: 7:

(i) SEQUENCE CHARACTERISTICS:
    (A) LENGTH: 226 Amino Acids
    (B) TYPE: Amino Acid
    (D) TOPOLOGY: Linear (xi) SEQUENCE DESCRIPTION: SEQ ID NO: 7:

```
Met  Gly  Asn  Leu  Arg  Ser  Ser  Phe  Val  Phe  Phe  Leu  Leu  Ala
                    5                   10

Leu  Val  Thr  Tyr  Thr  Tyr  Ala  Ala  Thr  Ile  Glu  Val  Arg  Asn
15                       20                      25

Asn  Cys  Pro  Tyr  Thr  Val  Trp  Ala  Ala  Ser  Thr  Pro  Ile  Gly
          30                  35                       40

Gly  Gly  Arg  Arg  Leu  Asp  Arg  Gln  Thr  Trp  Val  Ile  Asn
          45                      50                       55

Ala  Pro  Arg  Gly  Thr  Lys  Met  Ala  Arg  Val  Trp  Gly  Arg  Thr
               60                       65                        70

Asn  Cys  Asn  Phe  Asn  Ala  Ala  Gly  Arg  Gly  Thr  Cys  Gln  Thr
                    75                       80

Gly  Asp  Cys  Gly  Gly  Val  Leu  Gln  Cys  Thr  Gly  Trp  Gly  Lys
85                       90                       95

Pro  Pro  Asn  Thr  Leu  Ala  Glu  Tyr  Ala  Leu  Asp  Gln  Phe  Ser
     100                      105                      110

Gly  Leu  Asp  Phe  Trp  Asp  Ile  Ser  Leu  Val  Asp  Gly  Phe  Asn
          115                      120                      125

Ile  Pro  Met  Thr  Phe  Ala  Pro  Thr  Asn  Pro  Ser  Gly  Gly  Lys
               130                      135                       140

Cys  His  Ala  Ile  His  Cys  Thr  Ala  Asn  Ile  Asn  Gly  Glu  Cys
                    145                      150

Pro  Arg  Glu  Leu  Arg  Val  Pro  Gly  Gly  Cys  Asn  Asn  Pro  Cys
155                      160                      165

Thr  Thr  Phe  Gly  Gly  Gln  Gln  Tyr  Cys  Cys  Thr  Gln  Gly  Pro
     170                      175                           180

Cys  Gly  Pro  Thr  Phe  Phe  Ser  Lys  Phe  Phe  Lys  Gln  Arg  Cys
          185                      190                          195
```

```
Pro Asp Ala Tyr Ser Tyr Pro Gln Asp Asp Pro Thr Ser Thr
            200             205                 210

Phe Thr Cys Pro Gly Gly Ser Thr Asn Tyr Arg Val Ile Phe
                215             220

Cys Pro
225
```